(12) United States Patent
Hallinan et al.

(10) Patent No.: US 10,246,398 B2
(45) Date of Patent: Apr. 2, 2019

(54) ADDITIVES FOR CARBOXYLIC ACID PRODUCTION PROCESSES

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 15/340,716

(22) Filed: Nov. 1, 2016

(65) Prior Publication Data

US 2017/0144955 A1 May 25, 2017

Related U.S. Application Data

(60) Provisional application No. 62/260,001, filed on Nov. 25, 2015.

(51) Int. Cl.
*C07C 51/12* (2006.01)
(52) U.S. Cl.
CPC .................... *C07C 51/12* (2013.01)
(58) Field of Classification Search
CPC ....................................................... C07C 51/12
USPC ......................................................... 562/519
See application file for complete search history.

(56) References Cited

U.S. PATENT DOCUMENTS

2003/0130540 A1\* 7/2003 Tsai .................... C07C 51/12
562/519
2014/0120276 A1 5/2014 De Wolf et al.

OTHER PUBLICATIONS

The International Search Report and Written Opinion for PCT/US2016/059940 dated Jan. 26, 2017.

\* cited by examiner

*Primary Examiner* — Deborah D Carr

(57) ABSTRACT

Processes for producing carboxylic acid are included herein. The processes include contacting an alcohol and carbon monoxide in the presence of a liquid reaction medium under carbonylation conditions sufficient to form a carbonylation product including the carboxylic acid and recovering the carboxylic acid from the carbonylation product. The liquid reaction medium may include a carbonylation catalyst selected from rhodium catalysts, iridium catalysts and palladium catalysts; water in a water concentration ranging from 1 wt. % to 14 wt. % based on the total liquid reaction medium weight; and an additive, one or more in situ generated derivatives of the additive or combinations thereof, wherein the additive includes one or more salts of one or more compounds, each compound including at least one amino group and at least one acid group, the at least one acid group capable of forming an alkali metal salt.

5 Claims, 3 Drawing Sheets

ADDITIVES FOR CARBOXYLIC ACID PRODUCTION PROCESSES

CROSS-REFERENCE TO RELATED APPLICATIONS

This application claims the benefit of priority to U.S. Provisional Application No. 62/260,001, filed on Nov. 25, 2015, which is incorporated herein by reference in its entirety.

FIELD OF THE INVENTION

The present disclosure relates to carboxylic acid production processes. In particular, embodiments contained herein relate to additives for such processes.

BACKGROUND OF THE INVENTION

Carboxylic acids, such as acetic acid, may be commercially produced by alcohol carbonylation. Alcohol carbonylation processes may utilize a promoter, such as an alkyl iodide, in addition to a carbonylation catalyst. A consequence of iodide promoted reactions is that, in addition to the added alkyl iodide, variable concentrations of highly corrosive hydrogen iodide (HI) may be generated in situ. Continuous efforts have been directed towards reducing corrosion in carboxylic acid production processes. However, such efforts to reduce corrosion can result in catalyst stability concerns. Contained herein are embodiments directed to resolving, or at least reducing, one or all of the problems mentioned above.

SUMMARY OF THE INVENTION

The present disclosure provides for processes related to the production of carboxylic acids. The processes may include contacting an alcohol and carbon monoxide (CO) in the presence of a liquid reaction medium under carbonylation conditions sufficient to form a carbonylation product including the carboxylic acid and recovering the carboxylic acid from the carbonylation product. In some embodiments, the liquid reaction medium includes a carbonylation catalyst selected from rhodium catalysts, iridium catalysts and palladium catalysts; water in a concentration ranging from 1 wt. % to 14 wt. % based on the total liquid reaction medium weight; and an additive, one or more in situ generated derivatives of the additive or combinations thereof, wherein the additive includes one or more salts of one or more compounds, each compound including at least one amino group and at least one acid group, the at least one acid group capable of forming an alkali metal salt. In further embodiments, the alcohol is selected from methanol, ethanol, butanol, pentanol and combinations thereof.

One or more embodiments relate to processes for producing acetic acid. In some embodiments, the processes include contacting methanol and carbon monoxide in the presence of a liquid reaction medium under carbonylation conditions sufficient to form a carbonylation product including acetic acid and recovering acetic acid from the carbonylation product. In further embodiments, the liquid reaction medium includes a carbonylation catalyst selected from rhodium catalysts, iridium catalysts and palladium catalysts; water in a concentration ranging from 1 wt. % to 14 wt. % based on the total liquid reaction medium weight; and an additive, one or more in situ generated derivatives of the additive or combinations thereof, wherein the additive includes one or more salts of one or more compounds, each compound including at least one amino group and at least one acid group, the at least one acid group capable of forming an alkali metal salt. In still further embodiments, the at least one acid group includes sodium. In additional embodiments, the additive includes a di-sodium salt, a tri-sodium salt or combinations thereof.

In some embodiments, the additive includes a glutamate salt. In further embodiments, the additive includes a glutamate salt selected from N,N-bis(carboxymethyl)-DL-alanine trisodium salt, L-glutamic acid monosodium salt hydrate and combinations thereof. In still further embodiments, the additive includes a tyrosine salt. In additional embodiments, the additive includes L-3-(4-Hydroxyphenyl) alanine disodium salt. In additional embodiments, the reaction medium includes the additive in a concentration ranging from 0.005 M to 2.0 M. In certain embodiments, the reaction medium includes the additive in a concentration ranging from 0.05 M to 0.2 M.

In some embodiments, the acetic acid is glacial acetic acid. In further embodiments, the water concentration ranges from 1 wt. % to 10 wt. % water based on the total liquid reaction medium weight. In still further embodiments, the water concentration ranges from 1 wt. % to 6 wt. % based on the total liquid reaction medium weight. In additional embodiments, the carbonylation conditions include a carbonylation temperature ranging from 150° C. to 250° C. and a carbonylation pressure ranging from 200 psig (1379 kPa) to 2000 psig (13790 kPa).

In some embodiments, the present technology reduces the corrosion rate by at least 20% less as compared to an identical process absent the additive, one or more in situ generated derivatives of the additive or combinations thereof, including a 50% reduction, an 80% reduction and a 90% reduction. In certain embodiments, the reduction in corrosion occurs at an additive concentration of 0.1 M. In further embodiments, processes in accordance with the present technology exhibit a reaction rate that is at least 30% higher than that of an identical process absent the additive, one or more in-situ generated derivatives of the additive or combinations thereof. In still further embodiments, the reaction rate and the corrosion rate are achieved with a reaction medium comprising a single additive for inhibiting corrosion, improving catalyst stability or combinations thereof.

BRIEF DESCRIPTION OF THE DRAWINGS

The claimed subject matter may be understood by reference to the following description taken in conjunction with the accompanying drawings, in which like reference numerals identify like elements, and in which:

Figure 1:
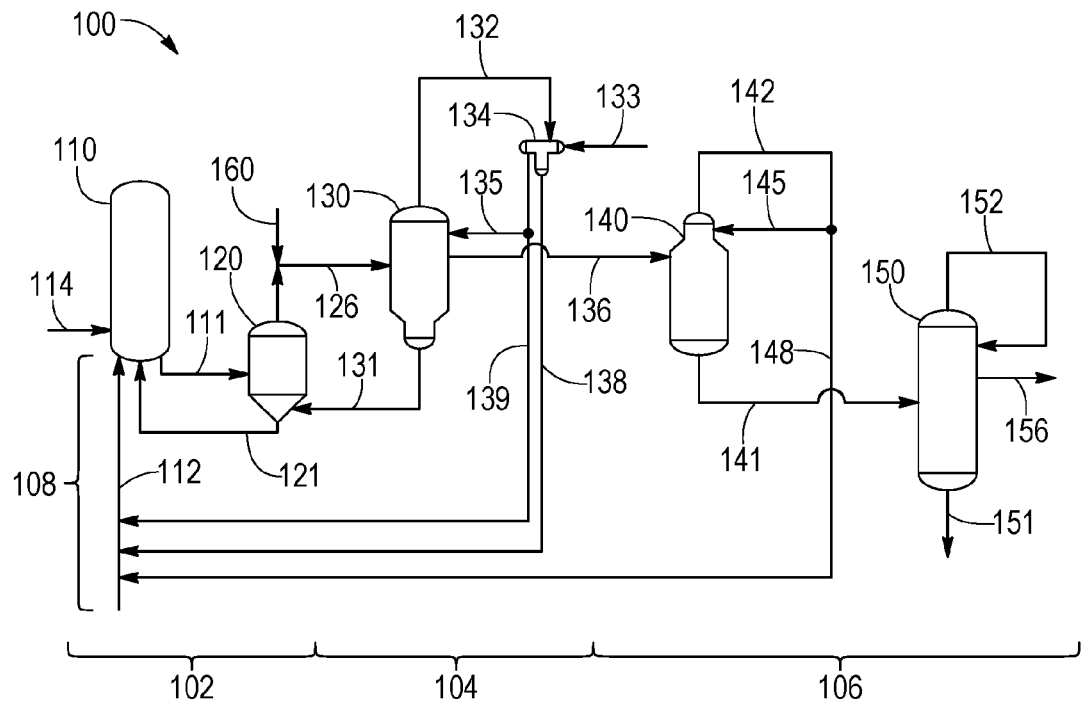
FIG. 1 illustrates a schematic of one or more embodiments of the disclosed processes.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover modifications, equivalents, and alternatives falling within the spirit and scope as defined by the appended claims.

DETAILED DESCRIPTION OF THE INVENTION

Illustrative embodiments of the subject matter claimed below will now be disclosed. In the interest of clarity, not every feature of an actual implementation is described in this specification. It will be appreciated that in the development of any such actual embodiment, numerous implementation-specific decisions can be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein refers to a value within a specified range and encompasses every value within that entire specified range.

Further, in the description below, unless otherwise specified, the compounds described herein may be substituted or unsubstituted and the listing of compounds includes derivatives thereof.

Embodiments described herein include processes for producing carboxylic acids. It will be realized that while specific embodiments herein may refer specifically to acetic acid production processes, it is to be understood by one skilled in the art that such embodiments may be utilized in other carboxylic acid production processes. For example, the embodiments described herein are also applicable to the carbonylation of higher homologues of methanol, such as ethanol, butanol and pentanol, to produce carboxylic acids therefrom. The adaptation of the embodiments to such systems will be readily apparent to the skilled artisan given the following discussion.

Furthermore, one or more specific embodiments include the production of glacial acetic acid (which is encompassed by the term "acetic acid" herein). Glacial acetic acid refers to acetic acid that is largely undiluted, e.g. a water concentration of no greater than about 0.15 wt. % based on the total weight of acetic acid and water.

One or more specific embodiments include acetic acid production processes. The acetic acid production processes may include carbonylation processes. For example, the acetic acid production processes may include the carbonylation of methanol and/or its derivatives to produce acetic acid.

The carbonylation processes utilized to produce acetic acid can include reacting an alcohol, such as methanol, with carbon monoxide in a reaction medium, such as a liquid reaction medium, under carbonylation conditions sufficient to form a carbonylation product including acetic acid and recovering the formed acetic acid from the carbonylation product. As described herein, the term "liquid reaction medium" refers to a reaction medium that is primarily liquid in form. For example, the liquid reaction medium may contain minor amounts of alternative phases. In one or more embodiments, the liquid reaction medium is at least 90%, or at least 91%, or at least 92%, or at least 93%, or at least 94%, or at least 95%, or at least 96%, or at least 97%, or at least 98%, or at least 99% liquid phase.

The reaction medium may include a carbonylation catalyst. Carbonylation catalysts include, but are not limited to, rhodium catalysts, iridium catalysts and palladium catalysts. Rhodium catalysts include rhodium metal and rhodium compounds selected from rhodium salts, rhodium oxides, rhodium acetates, organo-rhodium compounds, coordination compounds of rhodium and mixtures thereof as described, e.g. in U.S. Pat. No. 5,817,869, which is incorporated by reference in its entirety. Iridium catalysts include iridium metal and iridium compounds selected from iridium acetates, iridium oxalates, iridium acetoacetates and mixtures thereof as described, e.g. in U.S. Pat. No. 5,932,764, which is incorporated by reference in its entirety.

The concentration of carbonylation catalyst in the reaction medium may range from 1 millimolar (mmol) to 100 mmol, or from 2 mmol to 5 mmol, or at least 7.5 mmol, or from 2 mmol to 75 mmol, or from 5 mmol to 50 mmol, or from 7.5 mmol to 25 mmol of catalyst per liter of reaction medium.

In one or more embodiments, the carbonylation catalyst is utilized with a co-catalyst. The co-catalyst may be selected from metal and metal compounds including osmium, rhenium, ruthenium, cadmium, mercury, zinc, gallium, indium, tungsten, salts of these metals and mixtures of these metals and salts. In one or more embodiments, the metal compounds include metal acetates. The concentration of co-catalyst in the reaction medium may range from 500 ppm to 3000 ppm, or from 1000 ppm to 2000 ppm, based on the total reaction medium weight.

In one or more embodiments, the reaction medium further includes water. The concentration of water in the reaction medium may range from 1 wt. % to 14 wt. %, or 10 wt. % or less, or 8 wt. % or less, or 6 wt. % or less, or from 1 wt. % to 5 wt. %, or from 4 wt. % to 8 wt. % water based on the total reaction medium weight.

Furthermore, the reaction medium may include an alkyl acetate such as methyl acetate. The concentration of alkyl acetate in the reaction medium may range from 0.6 wt. % to 36 wt. %, or from 2 wt. % to 20 wt. %, or from 2 wt. % to 16 wt. %, or from 3 wt. % to 10 wt. %, or from 2 wt. % to 8 wt. % based on the total reaction medium weight.

In addition, it is contemplated that supplemental hydrogen may be supplied to the reaction medium. Supplemental hydrogen may be supplied to the reaction medium to provide a total hydrogen concentration in the gaseous component of the feedstock to the carbonylation reaction ranging from 0.1 mol. % to 5 mol. %, or from 0.3 mol. % to 3 mol. %.

In one or more embodiments, the reaction medium further includes one or more promoters. For example, the reaction medium may include an iodide promoter. The iodide promoter may include an alkyl iodide such as methyl iodide. The concentration of such promoters in the reaction medium may range from 0.6 wt. % to 36 wt. %, or from 4 wt. % to 24 wt. %, or from 6 wt. % to 20 wt. % based on the total reaction medium weight. The iodide promoter may be introduced to the reaction medium in a form such that the introduced compound will directly promote the carbonylation reaction, e.g. the introduction of methyl iodide to the carbonylation reaction. Alternatively, one or more compounds may be introduced to the reaction medium to form in situ generated compounds capable of promoting the carbonylation reaction. For example, carbonylation processes may introduce hydrogen iodide to the reaction medium and form methyl iodide as promoter. Unfortunately, hydrogen iodide is highly corrosive and therefore can be detrimental to the carbonylation process.

Thus, the reaction medium may further include a variety of additives or other components (e.g., components other than the alcohol, carbon monoxide, carbonylation catalyst, water and promoter). The introduction of such additives to the reaction medium can be via any previously disclosed or established method, e.g. each of the additives may be, either independently or as a mixture, introduced directly to the reaction medium. Alternatively, one or more of the additives may be generated in situ.

In the embodiments disclosed herein, the additives can include an additive (or in situ generated derivative of the additive) for providing catalyst stability, corrosion inhibition or a combination thereof to the process. It should be understood that the effect of the additives described herein may allow improved catalyst stabilization and improved corrosion inhibition. While the use of multiple additives to provide catalyst stability, corrosion inhibition, or a combination thereof within the same reaction medium is contemplated herein and within the scope of the technology, one or more embodiments provide a reaction medium including an additive (i.e., a single additive) for providing both catalyst stability and corrosion inhibition.

In the embodiments described herein, the additives include one or more salts of one or more compounds including at least one amino group and at least one acid group capable of forming an alkali metal salt (referred to interchangeably herein as additive salts). As used herein, the term "capable of forming an alkali metal salt" refers to an acid group having one or more components such that either before or upon reaction of the one or more compounds, an alkali metal salt is formed. In one or more embodiments, the at least one acid group includes an alkali metal. For example, the at least one acid group may include sodium. In one or more embodiments, the at least one acid group includes a plurality of alkali metals, either the same or different. For example, one or more specific embodiments may utilize a di-sodium salt, a tri-sodium salt or combinations thereof as the additive.

In some embodiments, the additive includes a tyrosine salt including but not limited to L-3-(4-hydroxyphenyl) alanine disodium salt. In one or more embodiments, the additive includes a glutamate salt. In certain embodiments, the glutamate salt includes di-sodium compounds, tri-sodium compounds or combinations thereof. Examples of glutamate salts include but are not limited to N,N-bis (carboxymethyl)-DL-alanine trisodium salt ("BCA"), L-glutamic acid monosodium salt hydrate ("LGA") and combinations thereof.

The concentration of additive salt in the reaction medium should be sufficient to function as intended, e.g. in corrosion inhibition and/or catalyst stability. For example, the total concentration of additive in the reaction medium may range from 0.05 molar (M) to 1.8 M, or from 0.1 M to 1.8 M, or from 0.2 M to 1.8 M, or from 0.25 M to 1.5 M, or from 0.5 M to 1.0 M (measured at cold degassed conditions). It is to be noted that the concentrations described herein refers to the total additive salt concentration present in the reaction medium.

It has been observed that the use of the additive salts described herein inhibit corrosion at an unexpected rate. For example, the process may exhibit corrosion at a rate (i.e., a "corrosion rate" measured as described in the examples that follow herein) that is at least 20%, or at least 30%, or at least 40%, or at least 50%, or at least 60%, or at least 70%, or at least 75%, or at least 80%, or at least 85%, or at least 90%, or at least 95%, or from 50% to 100%, or from 70% to 100% less than that of an identical process absent the additive, in situ generated derivatives of the additive or combinations thereof. In one or more particular embodiments, the process may exhibit a corrosion rate that is at least 90% less than that of an identical process absent the additive, in situ generated derivatives of the additive or combinations thereof at an additive concentration of 0.1 M.

The additives may be introduced to the reaction mixture via previously disclosed methods. For example, one or more specific embodiments include introduction of the additive to the reaction medium in solution form. Such a solution may include the additive dissolved with a solvent that will not react with the other components of the reaction medium, such as carboxylic acids, including, but not limited to acetic acid, water or combinations thereof. Alternative embodiments include introduction of the additive to the reaction medium directly (either in liquid or solid form).

It has further been observed that such decreased corrosion can be obtained without significantly decreasing the rate of reaction as identified by the rate constant, k, and determined by methods referenced in the examples below. In fact, such decreased corrosion can be obtained with the additives described herein while observing an improved rate of reaction. For example, such decreased corrosion rates may be observed with from a 30% to 100%, or from 35% to 95%, or from 40% to 90%, or from 45% to 85%, or from 50% to 80%, or from 55% to 75% increase in reaction rate compared to an identical process absent the additive, in situ generated derivatives of the additive or combinations thereof.

It has further been observed that the addition of the disclosed salts provide for the corrosion inhibition described herein while at the same time providing for the recited levels of catalyst stability without the need for secondary additives. In particular, improved corrosion inhibition as well as improved catalyst stability as evidenced by improved rates of reaction can be observed with embodiments utilizing a single additive compared to prior systems utilizing multiple additives to achieve a balance of corrosion inhibition and catalyst stability.

In practice, carbonylation reaction conditions vary depending upon reaction parameters, reactor size and charge and the individual components employed. However, in one or more embodiments, the carbonylation process may be a batch or continuous processes and the carbonylation conditions may include a carbonylation pressure ranging from 200 psig (1379 kPa) to 2000 psig (13790 kPa), or from 200 psig (1379 kPa) to 1000 psig (6895 kPa), or from 300 psig (2068 kPa) to 500 psig (3447 kPa), for example, and a carbonylation temperature ranging from 150° C. to 250° C., or from 170° C. to 220° C., or from 150° C. to 200° C.

Carbonylation processes further include recovering the formed acetic acid from carbonylation product. Such recovery can be accomplished by methods which may include separation and/or purification processes including but not limited to flashing and distillation. Such processes are known to one skilled in the art and therefore are not described in detail herein.

FIG. 1 illustrates a schematic of an embodiment of a specific, non-limiting embodiment of a carboxylic acid production process 100. The process 100 may be described in terms of functional areas, i.e., a reaction area 102, a light-ends area 104, a purification area 106 and a recycle area 108, rather than specific process equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and flash vessel 120. For example, the reaction area 102 may include reactor 110, flash vessel 120, and streams (or portions of streams) 111, 112, 114, 121, 126, 131, 160, 138, 139 and 148. The reactor 110 is a reactor or vessel in which an alcohol is carbonylated in the presence of a carbonylation catalyst to form a carboxylic acid at elevated pressure and temperature. The flash vessel 120 is a tank or vessel in which a reaction mixture obtained in the reactor, for example the reactor 110, is at least partially depressurized and/or cooled to form a vapor stream and a liquid stream.

The light-ends area 104 may include a separation column, a light-ends column 130, equipment associated with light-ends column 130 and streams associated with the light-ends column 130. For example, the light-ends area 104 may include light-ends column 130, decanter 134, and streams 126, 131, 132, 133, 135, 136, 138, 139 and 160. The light-ends column 130 is a fractioning or distillation column and includes any equipment associated with the column, including but not limited to heat exchangers, decanters, pumps, compressors and valves.

The purification area 106 may include a drying column 140, optionally, a heavy-ends column 150, equipment associated with drying column 140 and heavy-ends column 150, and streams associated with the drying column 140 and heavy-ends column 150. For example, the purification area 106 may include drying column 140, heavy-ends column 150, and streams 136, 141, 142, 145, 148, 151, 152, 156. The heavy-ends column 150 is a fractioning or distillation column and includes any equipment associated with the column, including but not limited to heat exchangers, decanters, pumps, compressors and valves.

The recycle area 108 may include process streams recycled to the reaction area 102 and/or light-ends area 104. For example, in FIG. 1, the recycle area 108 may include streams 121, 138, 139 and 148.

In one or more embodiments, the reactor 110 may be configured to receive a carbon monoxide feed stream 114 and a methanol or methanol/methyl acetate feed stream 112. A reaction mixture may be withdrawn from the reactor in stream 111. Other streams may be included, for example, a stream that may recycle a bottoms mixture of the reactor 110 back into the reactor 110, or a stream may be included to release a gas from the reactor 110. Stream 111 may include at least a part of the reaction mixture.

In one or more embodiments, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110 (stream 121 may thus be considered in the recycle area 108 and in the reactor area 102). In one or more embodiments, stream 126 may include acetic acid, water, methyl iodide, methyl acetate, HI, and mixtures thereof, for example.

In an embodiment, the light-ends column 130 may include a distillation column and equipment associated with the distillation column including but not limited to a heat exchanger 137, a decanter 134, pumps, compressors and valves. The light-ends column 130 may be configured to receive stream 126 from the flash vessel 120. Stream 132 includes overhead product from the light-ends column 130, and stream 131 includes bottoms product from the light-ends column 130. Light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor (stream 138 may thus be considered in the recycle area 108, in the light-ends area 104, and in the reactor area 102). Stream 139 may recycle a portion of the light phase of decanter 134 back to the reactor 110 via, for example, stream 112 (stream 139 may thus be considered in the recycle area 108, in the light-ends area 104, and in the reactor area 102). Stream 136 may emit from the light-ends column 130. Other streams may be included, for example, a stream that may recycle a bottoms mixture of the light-ends column 130 back into the light-ends column 130. Any stream received by or emitted from the light-ends column 130 may pass through a pump, compressor, heat exchanger, and the like as is common in the art.

In an embodiment, the drying column 140 may comprise a vessel and equipment associated with the vessel including but not limited to heat exchangers, decanters, pumps, compressors and valves. The drying column 140 may be configured to receive stream 136 from the light-ends column 130. The drying column 140 may separate components of stream 136 into streams 142 and 141.

Stream 142 may emit from the drying column 140, recycle back to the drying column via stream 145, and/or recycle back to the reactor 110 through stream 148 via, for example, stream 112. Stream 141 may emit from the drying column 140 and may include de-watered crude acetic acid product. Stream 142 may pass through equipment that is readily available, for example, a heat exchanger or separation vessel before streams 145 or 148 recycle components of stream 142. Other streams may be included, for example, a stream may recycle a bottoms mixture of the drying column 140 back into the drying column 140. Any stream received by or emitted from the drying column 140 may pass through a pump, compressor, heat exchanger, separation vessel, and the like as is common in the art.

The heavy-ends column 150 may include a distillation column and equipment associated with the distillation column including but not limited to heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 140. Stream 156 may include acetic acid product. Alternative embodiments for the carboxylic acid production system 100 may be found in U.S. Pat. No. 6,552,221, which is incorporated in its entirety herein.

EXAMPLES

To facilitate a better understanding of the disclosure, the following examples of embodiments are given. In no way should the following examples be read to limit, or to define, the scope of the appended claims.

Corrosion Study Test Procedure: Samples of various additives/solutions (including the components of the liquid reaction medium (absent the carbonylation catalyst, methyl iodide and methanol) and plus or minus various additives as specified in Table 1 below) were added to 5 mL heavy walled borosilicate Wheaton vials such that the vials contained a total liquid volume of 4 mL. A glass bead blasted 316L stainless steel coupon of dimensions 0.062" (0.157 cm)×0.30" (0.762 cm)×0.50" (1.27 cm) and of approximately 1 gram in weight was added to each vial. Prior to addition to the vial, the coupons were cleaned by immersion in acetone for 5 minutes, followed by drying and weighing on a 4-figure analytical balance. These vials, charged with liquid and coupon, were then septum sealed and purged with one atmosphere of CO or $N_2$ for two (2) minutes followed by placement in a water bath maintained at the specified temperature. After 44-48 hours of heating, the vials were removed from the water bath and allowed to cool. The coupons were removed, soaked in acetone for 5 minutes, dried and re-weighed. The percent weight loss of coupons due to corrosion was calculated based on the initial and final weights.

Catalyst Stability Test Procedure: Studies were undertaken to analyze catalyst stability in terms of extent of decay of soluble Rh(I) to Rh(III). The rate and extent of Rh(I) decay in catalyst solutions maintained under flash tank conditions was monitored by periodic sampling and FTIR analysis. In such a procedure, a stock solution of the active rhodium catalyst was prepared by adding 0.20 g of rhodium (I) dicarbonyl chloride dimer, to 20 ml of acetic acid (HOAc) and saturating the solution with CO by bubbling one atmosphere of CO through the solution at room temperature for 5 minutes. 0.40 g of lithium iodide (LiI) was then added and after 10 minutes of stirring, the active Rh catalyst, $[Rh(CO)_2I_2]^-$ formed in quantitative yield. In the present examples, a solution of about 5,000 ppm resulted.

Example 1

A variety of samples were prepared and studied for corrosion. The data included in Table 1 shows coupon % weight loss data (determined via the Corrosion Study Test Procedure included above) for control experiments in which no additive/potential corrosion inhibitor was present (identified as a 0 in the concentration of additive) and for additional repeat experiments with various additives at the specified concentrations ranging from about 0.01 M to about 0.1 M. In order to replicate a carbonylation reaction environment, the vials further included hydrogen iodide as indicated in the table. Data from these experiments show a consistent trend in which the extent of corrosion is always greatest when no additive is present. For comparative purposes and to ensure maximum accuracy, a control vial containing no additive was typically included in each sample run. Therefore, data sometimes includes slightly differing values for the control experiment.

TABLE 1

| Sample # | BCA, M | LGA, M | % wt. loss |
|---|---|---|---|
| 1 | 0 | 0 | 0.901 |
| 2 | 0 | 0 | 0.886 |
| 3 | 0.011 | 0 | 0.784 |
| 4 | 0.024 | 0 | 0.616 |

TABLE 1-continued

| Sample # | BCA, M | LGA, M | % wt. loss |
|---|---|---|---|
| 5 | 0.05 | 0 | 0.610 |
| 6 | 0.117 | 0 | 0.009 |
| 7 | 0 | 0.011 | 0.722 |
| 8 | 0 | 0.023 | 0.776 |
| 9 | 0 | 0.068 | 0.818 |
| 10 | 0 | 0.104 | 0.778 |
| 11 | 0.021 | 0.031 | 0.856 |
| 12 | 0.092 | 0.085 | 0.027 |

*Note 1:
Testing conditions: 0.5M HI, 8 wt. % $H_2O$, HOAc, 70° C., 1 atm $N_2$, 44 hrs
*Note 2:
N,N-bis(carboxymethyl)-DL-alanine trisodium salt (i.e., BCA) was utilized as a 40% aqueous solution. Therefore, to ensure a constant water concentration in all samples, water was added as necessary to ensure that all vials contained 8 wt. % total water concentration.

Figure 2:
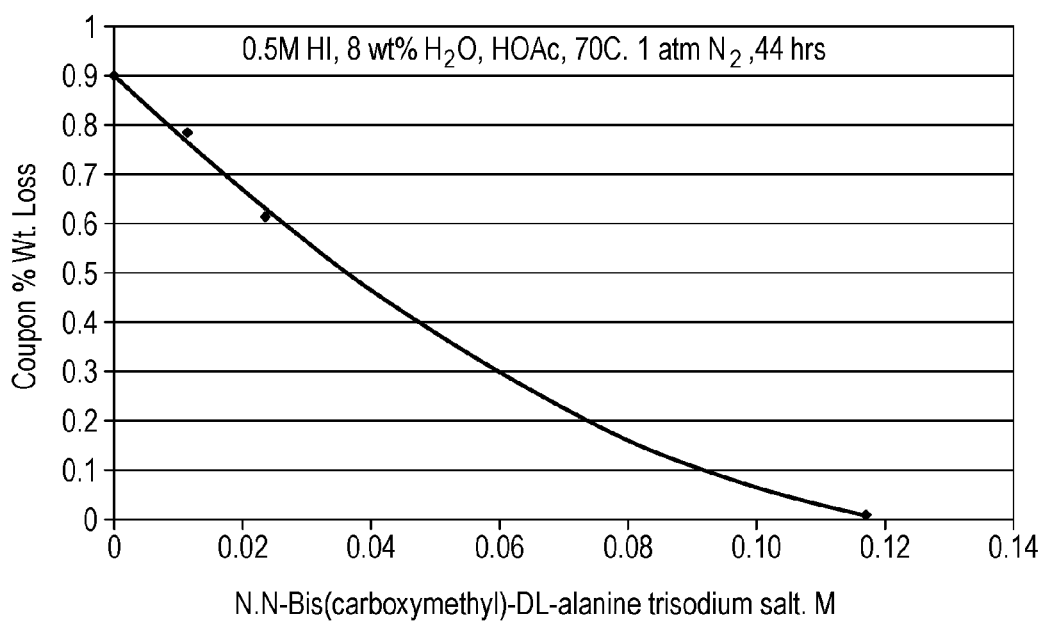
FIG. 2 illustrates additive concentration versus corrosion results associated with examples utilizing embodiments of the disclosed processes.

The data in Table 1 shows that the addition of additive decreased corrosion in all cases. However, at a concentration of about 0.1 M, the tri-sodium salt (N,N-bis(carboxymethyl)-DL-alanine trisodium salt) decreased corrosion by about 3 orders of magnitude compared to the samples having no additive. A correlation of the tri-sodium salt concentration with the extent of corrosion is shown in FIG. 2, in which a polynomial fit was applied.

Example 2

A series of runs were carried out to compare the ability of individual additives to stabilize active catalyst as described in the Catalyst Stability Test Procedures described previously herein. The runs were carried out with a variety of samples such as those utilized for the corrosion studies of Example 1. The data included in Table 2 shows rate constant ($k^{-1}$) for control experiments in which no additive/potential corrosion inhibitor was present (identified as a 0 in the concentration of additive) and for additional repeat experiments with various additives at the specified concentrations. It is to be noted that an increasing rate constant equals increasing catalyst degradation/loss of catalyst stability.

TABLE 2

| Additive | Conc., M | $k^{-1}$ |
|---|---|---|
| None | N/A | 0.217 |
| TPPO | 0.099 | 0.153 |
| Cyanex ® 923 | 0.097 | 0.07 |
| BCA | 0.02 | 0.132 |
| BCA | 0.031 | 0.071 |
| BCA | 0.117 | 0.024 |
| LGA | 0.044 | 0.131 |
| LGA | 0.099 | 0.129 |
| LGA | 0.297 | 0.050 |

*Note 1:
Testing conditions: 0.5M HI, 8 wt. % $H_2O$, HOAc, 70° C., 1 atm $N_2$, 44 hrs
*Note 2:
N,N-bis(carboxymethyl)-DL-alanine trisodium salt (i.e., BCA) was utilized as a 40% aqueous solution. Therefore, to ensure a constant water concentration in all samples, water was added as necessary to ensure that all vials contained 8 wt. % total water concentration.
Note 3:
TPPO refers to tri-phenyl phosphine oxide, a comparative additive.

Figure 3:
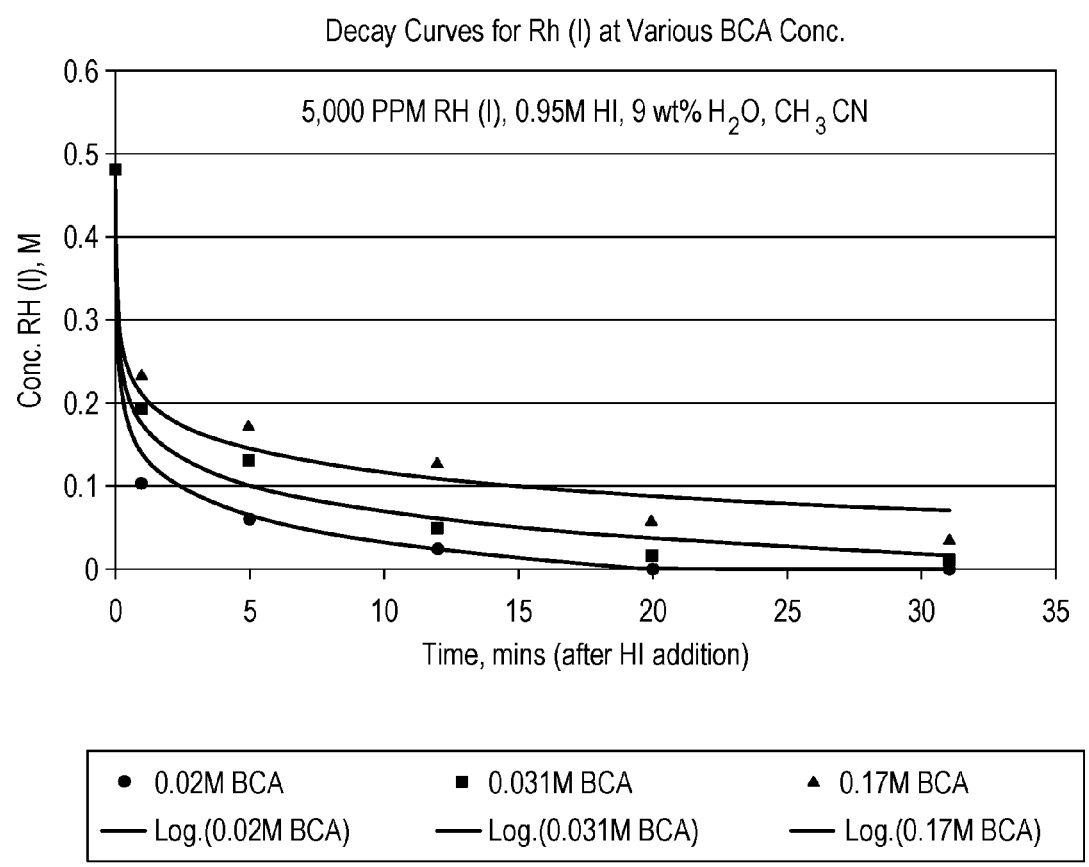
FIG. 3 illustrates catalyst decay curves associated with examples utilizing embodiments of the disclosed processes.
Figure 4:
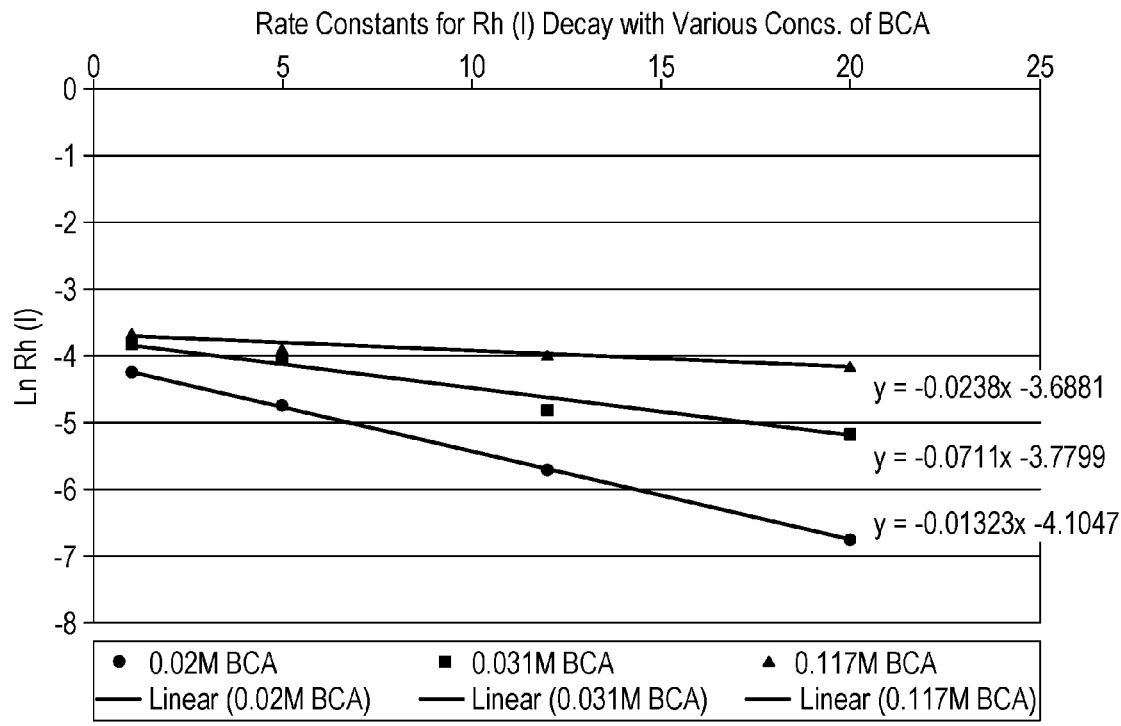
FIG. 4 illustrates rate curves associated with examples utilizing embodiments of the disclosed processes.
Figure 5:
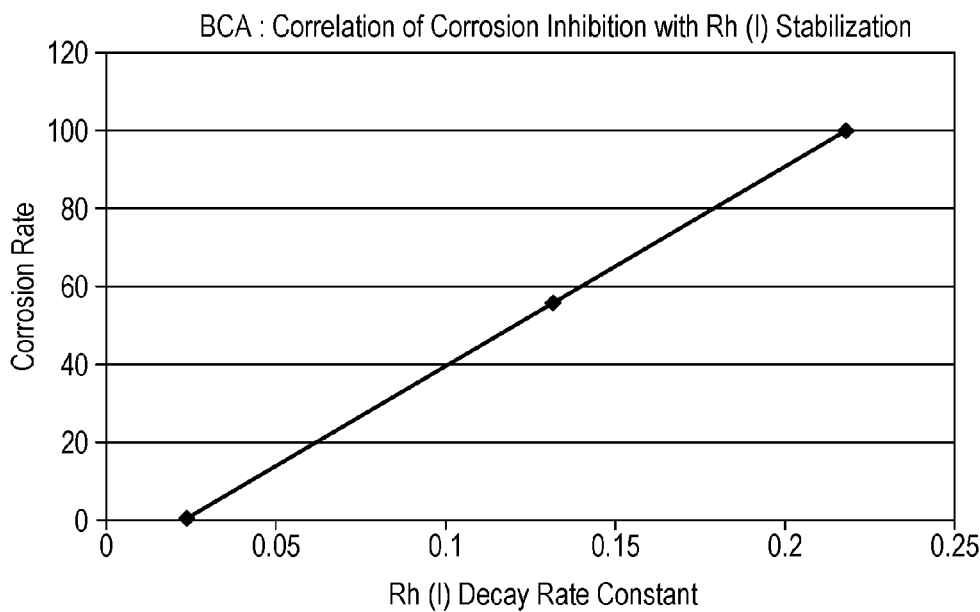
FIG. 5 illustrates corrosion versus catalyst stability results associated with examples utilizing embodiments of the disclosed processes.

Catalyst decay and rate constant curves for BCA were correlated from the data of Table 2 and are illustrated in FIGS. 3 and 4. Such curves show that up to a 10 fold increase in catalyst stabilization was obtained. In addition, a direct and favorable correlation of corrosion inhibition with catalyst stabilization were correlated and observed as illustrated in FIG. 5.

What is claimed is:

1. A process comprising:
contacting methanol and carbon monoxide in the presence of a liquid reaction medium under carbonylation conditions sufficient to form a carbonylation product comprising acetic acid, wherein the liquid reaction medium comprises:
  a carbonylation catalyst selected from rhodium catalysts, iridium catalysts and palladium catalysts;
  1-6 wt. % water, based on the total liquid reaction medium weight; and
  0.05-2.0 M of an additive selected from di-sodium glutamate salts, tri-sodium glutamate salts, di-sodium L-3-(4-hydroxyphenyl) alanine, tri-sodium N,N-bis(carboxymethyl)-DL-alanine, and combinations thereof; and
recovering acetic acid from the carbonylation product.

2. The process of claim 1, wherein the concentration of carbonylation catalyst in the reaction comprises 1-100 mmol of catalyst per liter of reaction medium.

3. The process of claim 1, wherein the concentration of carbonylation catalyst in the reaction comprises 2-5 mmol of catalyst per liter of reaction medium.

4. The process of claim 1, wherein the reaction medium comprises a liquid phase of 90-99%.

5. The process of claim 1, wherein the reaction medium comprises 0.6-36% by weight of an alkyl acetate.

* * * * *